United States Patent
Donnelly et al.

(10) Patent No.: US 9,012,383 B2
(45) Date of Patent: Apr. 21, 2015

(54) MOLYBDENUM DIALKYLDITHIOCARBAMATE COMPOSITIONS AND LUBRICATING COMPOSITIONS CONTAINING THE SAME

(75) Inventors: Steven G. Donnelly, Bethel, CT (US); Gaston A. Aguilar, Milford, CT (US); Kevin J. Chase, Branford, CT (US); William T. Wallack, Stamford, CT (US)

(73) Assignee: Vanderbilt Chemicals, LLC, Norwalk, CT (US)

( * ) Notice: Subject to any disclaimer, the term of this patent is extended or adjusted under 35 U.S.C. 154(b) by 490 days.

(21) Appl. No.: 13/425,560

(22) Filed: Mar. 21, 2012

(65) Prior Publication Data
US 2012/0264666 A1 Oct. 18, 2012

Related U.S. Application Data

(60) Provisional application No. 61/476,060, filed on Apr. 15, 2011, provisional application No. 61/510,544, filed on Jul. 22, 2011.

(51) Int. Cl.
*C10M 135/18* (2006.01)
*C07F 11/00* (2006.01)
*C10M 139/00* (2006.01)

(52) U.S. Cl.
CPC ...... *C10M 135/18* (2013.01); *C10M 2205/0285* (2013.01); *C10M 2219/068* (2013.01); *C10M 2227/066* (2013.01); *C10N 2230/70* (2013.01); *C10N 2240/10* (2013.01); *C10N 2270/00* (2013.01); *C07F 11/005* (2013.01); *C10M 139/00* (2013.01); *C10N 2220/028* (2013.01)

(58) Field of Classification Search
None
See application file for complete search history.

(56) References Cited

U.S. PATENT DOCUMENTS

| 5,627,146 | A | 5/1997 | Tanaka et al. |
| 6,245,725 | B1 | 6/2001 | Tanaka et al. |
| 2007/0249852 | A1 | 10/2007 | McClain et al. |
| 2007/0265176 | A1 | 11/2007 | Poirier et al. |
| 2014/0045737 | A1 | 2/2014 | Zhang et al. |

*Primary Examiner* — Vishal Vasisth
(74) *Attorney, Agent, or Firm* — Norris McLaughlin & Marcus P.A.

(57) ABSTRACT

A novel molybdenum dithiocarbamate composition is produced by preparing a di-tridecylamine (DTDA) intermediate from a butylene feedstock comprising greater than 50% 2-butylene, and preparing a molybdenum dithiocarbamate composition from the DTDA intermediate. The resulting molybdenum dithiocarbamate composition are according to formula (1), wherein $R_1$ to $R_4$ are $C_{11}$-$C_{14}$ isoalkyl groups, and X represents oxygen and/or sulfur atoms, and $R_1$ to $R_4$ comprise, on average, greater than 98% $C_{13}$:

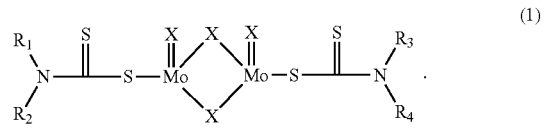

(1)

5 Claims, 1 Drawing Sheet

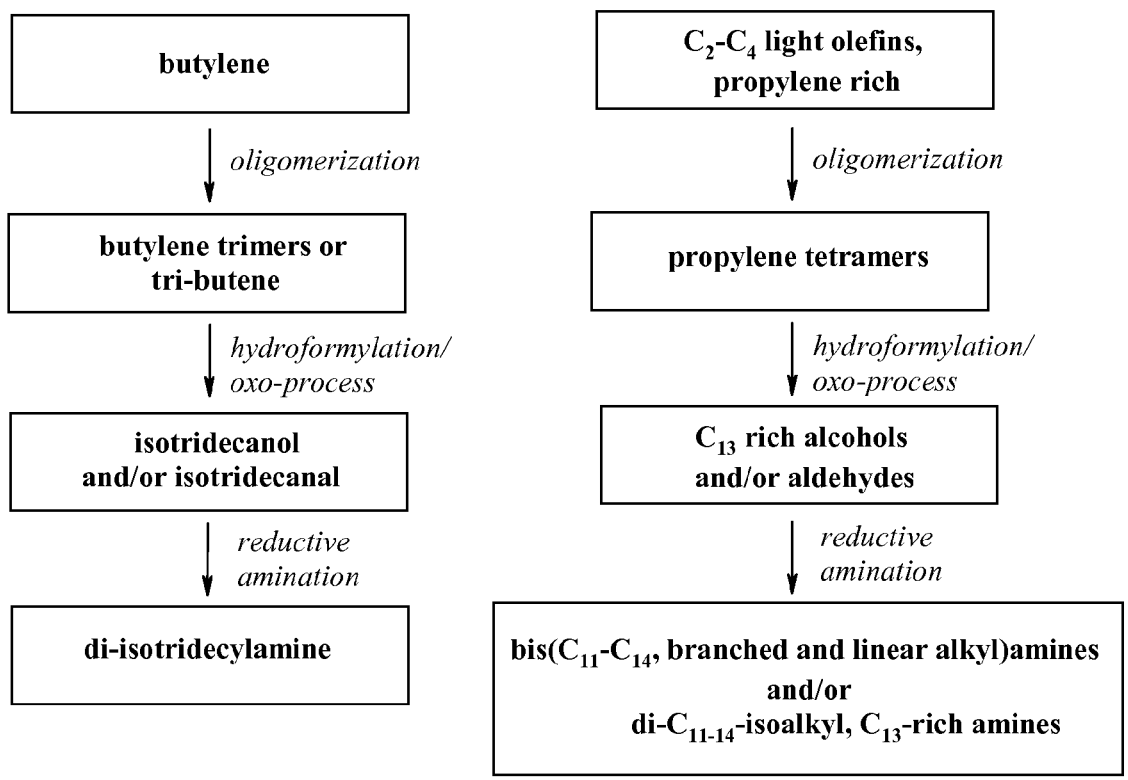

US 9,012,383 B2

MOLYBDENUM DIALKYLDITHIOCARBAMATE COMPOSITIONS AND LUBRICATING COMPOSITIONS CONTAINING THE SAME

This application claims benefit of 61/476,060, filed Apr. 15, 2011 and claims benefit of 61/510,544, filed Jul. 22, 2011.

BACKGROUND OF THE INVENTION

1. Field of the Invention

The invention relates to novel molybdenum dialkyldithiocarbamate compositions with improved oil solubility.

2. Discussion of the Prior Art

Molybdenum dialkyldithiocarbamate (MoDTC) compositions of formula (1) wherein $R_1$ to $R_4$ are isotridecyl groups or mixtures of $C_{11}$-$C_{14}$ isoalkyl groups, and X represents oxygen and/or sulfur atoms, are well-known lubricant additives that impart antifriction, antiwear and antioxidant properties:

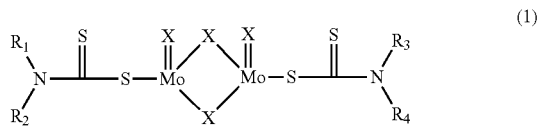

(1)

While MoDTC compositions of formula (1) have excellent antifriction, antiwear and antioxidant properties, they are known to lack oil solubility in high viscosity index oils and/or at lower temperatures, resulting in the formation of a haze, cloudiness or precipitate, which reduces lubricant effectiveness. For example in U.S. Pat. Nos. 5,627,146 and 6,245,725, Tanaka et al. teaches that MoDTC composition produced using di-2-ethylhexylamine and di-isotridecylamine (DTDA) have significantly improved oil solubility over MoDTC compositions produced from just DTDA.

In the disclosure herein, the inventors have surprisingly discovered MoDTC compositions with improved oil solubility can be produced from particular DTDA compositions. Specifically, the inventors found that MoDTC compositions produced from DTDA derived from oligomerization of butylene feedstocks composed of major amount (>50%) of 2-butylene and minor amounts of 1-butylene and/or isobutylene, and as a result of which have on average greater than 98% of $C_{13}$ present as the constituent R groups, have improved oil solubility in high viscosity index oils and/or at lower temperatures over MoDTC compositions produced from other DTDA compositions known in the art, in particular di-$C_{11-14}$-isoalkyl, $C_{13}$-rich amines; and bis($C_{11}$-$C_{14}$, branched and linear alkyl)amines. It should be noted that in this art di-$C_{11-14}$-isoalkyl, $C_{13}$-rich amines; and bis($C_{11}$-$C_{14}$, branched and linear alkyl)amines are also commonly, though inaccurately, referred to as DTDA, and have on average no more than 73% of $C_{13}$ present as the constituent R groups.

SUMMARY OF THE INVENTION

As summarized in Scheme 1, the basic building block for DTDA compositions are light olefin feedstocks that are mainly composed of either butylene or propylene gas. To build DTDA alkyl chains, the butylene and propylene rich light olefin feedstocks are oligomerized to isomeric dodecene mixtures that are generally referred to as butylene trimers and propylene tetramers respectively. The resulting higher olefin compositions are then converted to $C_{13}$ or $C_{13}$-rich alcohols and/or aldehydes via hydroformylation reaction in which olefins react with carbon monoxide and hydrogen in presence of either cobalt or rhodium catalysts. On an industrial scale, hydroformylation of olefins is referred to as oxo-synthesis or oxo-process and resulting alcohol compositions are commonly referred to as oxo-alcohols. In the art, $C_{13}$ and $C_{13}$-rich oxo-alcohols are commonly referred to as isotridecanol. The final step in the scheme is the conversion of the alcohol and/or aldehyde compositions to DTDA by a process known as reductive amination. For this invention, MoDTCs are produced by this sequence of chemical transformation using butylene feedstocks composed of major amount (>50%) of 2-butylene and minor amounts of 1-butene and/or isobutene The invention also relates to a method for making a novel molybdenum dithiocarbamate composition and to lubricating compositions containing an effective amount of the inventive molybdenum di-isotridecyldithiocarbamate composition. The inventive additives have improved solubility, especially in high viscosity index oils and/or at lower temperatures. In particular, the invention relates to novel molybdenum dialkyldithiocarbamates prepared from butylene-derived DTDA, which have on average greater than 98% $C_{13}$ as part of the constituent R groups. It is noted that, the claimed MoDTC composition will be composed of MoDTC molecules, which may vary in the alkyl R group structure, though the average of the composition as a whole will be greater than 98% $C_{13}$.

BRIEF DESCRIPTION OF THE DRAWING

The FIGURE is a flow diagram for production of di-isotridecylamine (DTDA) compositions starting from both butylene and propylene-rich feedstocks.

DETAILED DESCRIPTION OF THE INVENTION

The inventive MoDTC compositions are prepared by any of a number of methods known to those skilled in the art, such as, but not limited to, the reaction of molybdenum trioxide, water, carbon disulfide and dialkylamines. Examples of other methods are described in U.S. Pat. Nos. 3,356,702; 3,509,051; 4,098,705; 4,178,258; 5,631,213; 7,312,348; 7,524,799; and 7,858,655.

Critical to this invention is the dialkylamine starting material. Specifically, the amine should be DTDA that originates from butylene gas feedstock, which is $C_4$ olefin mixture composed of cis-2-butylene, trans-2-butylene, 1-butylene and isobutylene. It is noted that trace amounts of other olefins, such as ethylene, propylene and pentene may be present in the feedstock. To build iso-tridecyl chains, butylene feedstock is first oligomerized to tri-butylene, an isomeric mixture of dodecene molecules. After the butylene oligomerization, the resulting trimer is converted to iso-tridecanal and/or iso-tridecanol by hydroformylation or the oxo-process, as it is known in the chemical industry. The final step is the conversion of the iso-tridecanal and/or iso-tridecanol to DTDA by reductive amination. In reductive amination, aldehydes and/or alcohols compositions react either with ammonia, primary amines or secondary amines to produce imines intermediates that are then reduced by catalytic hydrogenation to primary, secondary and tertiary amines respectively. In the case of dialkylamines such di-isotridecylamine, the aminating agent is ammonia and iso-tridecanal and/or iso-tridecanol first form the primary amine or isotridecylamine. The isotridecylamine then reacts further with iso-tridecanal and/or iso-tridecanol to give corresponding di-isotridecyamine, which in turn can react again with and iso-tridecanal and/or iso-tridecanol to form tri-isotridecyamine. Depending on the composition of the reaction batch and other reaction conditions such as pressure, temperature and reaction time, the process can be controlled to preferably produced DTDA.

To improve antioxidant, antiwear and antifriction, compositions of the invention may be incorporated in the lubricating compositions by known methods in an amount effective to produce the desired characteristics. In preferred embodiment of the invention, the amount may range from about 0.01 to 3.0 percent by weight based on the total weight of the lubricating composition, preferably about 0.1-1%, and most preferably about 0.25-5%.

The base oils employed as lubricant vehicles are typical oils used in automotive and industrial applications such as, among others, turbine oils, hydraulic oils, gear oils, crankcase oils and diesel oils. Natural base oils include mineral oils, petroleum oils, paraffinic oils and the vegetable oils. The base oil may also be selected from oils derived from petroleum hydrocarbon and synthetic sources. The hydrocarbon base oil may be selected from naphthenic, aromatic, and paraffinic mineral oils. The synthetic oils may be selected from, among others, ester-type oils (such as silicate esters, pentaerythritol esters and carboxylic acid esters), hydrogenated mineral oils, silicones, silanes, polysiloxanes, alkylene polymers, and polyglycol ethers.

The lubricating compositions optionally contain the necessary ingredients to prepare the composition, as for example dispersing agents, emulsifiers, and viscosity improvers. Depending on the intended use of the lubricant, other functional additives may be added to enhance a particular property of the lubricant. The lubricating compositions may also contain one or more of the following additives:

1. Borated and/or non-borated dispersants
2. Additional antioxidant compounds
3. Seal swell compositions
4. Friction modifiers
5. Extreme pressure/antiwear agents
6. Viscosity modifiers
7. Pour point depressants
8. Detergents
9. Phosphates
10. Antifoamants
11. Rust inhibitors
12. Copper corrosion inhibitors
1. Borated and/or Non-Borated Dispersants Non-borated ashless dispersants may be incorporated within the final fluid composition in an amount comprising up to 10 weight percent on an oil-free basis. Many types of ashless dispersants listed below are known in the art. Borated ashless dispersants may also be included.

(A) "Carboxylic dispersants" are reaction products of carboxylic acylating agents (acids, anhydrides, esters, etc.) containing at least about 34 and preferably at least about 54 carbon atoms reacted with nitrogen-containing compounds (such as amines), organic hydroxy compounds (such aliphatic compounds including monohydric and polyhydric alcohols, or aromatic compounds including phenols and naphthols), and/or basic inorganic materials. These reaction products include imide, amide and ester reaction products of carboxylic acylating agents. Examples of these materials include succinimide dispersants and carboxylic ester dispersants. The carboxylic acylating agents include alkyl succinic acids and anhydrides wherein the alkyl group is a polybutyl moiety, fatty acids, isoaliphatic acids (e.g., 8-methyloctadecanoic acid), dimer acids, addition dicarboxylic acids, addition (4+2 and 2+2) products of an unsaturated fatty acid with an unsaturated carboxylic reagent), trimer acids, addition tricarboxylic acids (e.g., Empol® 1040, Hystrene® 5460 and Unidyme® 60), and hydrocarbyl substituted carboxylic acylating agents (from olefins and/or polyalkenes). In one preferred embodiment, the carboxylic acylating agent is a fatty acid. Fatty acids generally contain from about 8 up to about 30, or from about 12 up to about 24 carbon atoms. Carboxylic acylating agents are taught in U.S. Pat. Nos. 2,444,328, 3,219, 666 and 4,234,435, which are incorporated herein by reference. The amine may be a mono- or polyamine. The monoamines generally have at least one hydrocarbyl group containing 1 to about 24 carbon atoms, with from 1 to about 12 carbon atoms. Examples of monoamines include fatty ($C_8$-$C_{30}$) amines, primary ether amines, tertiary-aliphatic primary amines, hydroxyamines (primary, secondary or tertiary alkanol amines), ether N-(hydroxyhydrocarbyl)amines, and hydroxyhydrocarbyl amines. The polyamines include alkoxylated diamines, fatty diamines, alkylenepolyamines (ethylenepolyamines), hydroxy-containing polyamines, polyoxyalkylene polyamines, condensed polyamines (a condensation reaction between at least one hydroxy compound with at least one polyamine reactant containing at least one primary or secondary amino group), and heterocyclic polyamines. Useful amines include those disclosed in U.S. Pat. No. 4,234,435 and U.S. Pat. No. 5,230,714 that are incorporated herein by reference. Examples of these "carboxylic dispersants" are described in British Patent 1,306,529 and in U.S. Pat. Nos. 3,219,666, 3,316,177, 3,340,281, 3,351,552, 3,381,022, 3,433,744, 3,444,170, 3,467,668, 3,501,405, 3,542,680, 3,576,743, 3,632,511, 4,234,435, and Re 26,433, which are incorporated herein by reference for disclosure of dispersants.

(B) "Amine dispersants" are reaction products of relatively high molecular weight aliphatic or alicyclic halides and amines, preferably polyalkylene polyamines. Examples thereof are described, for example, in U.S. Pat. Nos. 3,275, 554, 3,438,757, 3,454,555, and 3,565,804, which are incorporated herein by reference for disclosure of dispersants.

(C) "Mannich dispersants" are the reaction products of alkyl phenols in which the alkyl group contains at least about 30 carbon atoms with aldehydes (especially formaldehyde) and amines (especially polyalkylene polyamines). The materials described in U.S. Pat. Nos. 3,036,003, 3,236,770, 3,414, 347, 3,448,047, 346,172, 3,539,633, 3,586,629, 3,591,598, 3,634,515, 3,725,480, and 3,726,882 are incorporated herein by reference for disclosure of dispersants.

(D) Post-treated dispersants are obtained by reacting carboxylic, amine or Mannich dispersants with reagents such as urea, thiourea, carbon disulfide, aldehydes, ketones, carboxylic acids, hydrocarbon-substituted succinic anhydrides, nitriles, epoxides, boron compounds, phosphorus compounds, molybdenum compounds, tungsten compounds or the like. U.S. Pat. Nos. 3,200,107, 3,282,955, 3,367,943, 3,513,093, 3,639,242, 3,649,659, 3,442,808, 3,455,832, 3,579,450, 3,600,372, 3,702,757, 3,708,422, 4,259,194, 4,259,195, 4,263,152, 4,265,773, 7,858,565 and 7,879,777 are incorporated herein by reference for disclosure of dispersants.

(E) Polymeric dispersants are interpolymers of oil-solubilizing monomers such as decyl methacrylate, vinyl decyl ether and high molecular weight olefins with monomers containing polar substituents, e.g., aminoalkyl acrylates or acrylamides and poly-(oxyethylene)-substituted acrylates. Polymer dispersants are disclosed in U.S. Pat. Nos. 3,329,658, 3,449,250, 3,519,656, 3,666,730, 3,687,849, and 3,702,300, which are incorporated herein by reference for disclosure of dispersants and ashless dispersants.

Borated dispersants are described in U.S. Pat. Nos. 3,087, 936 and 3,254,025, which are incorporated herein by reference for disclosure of borated dispersants.

Also included, as possible dispersant additives are those disclosed in U.S. Pat. Nos. 5,198,133 and 4,857,214, which are incorporated herein by reference. The dispersants of these patents compare the reaction products of an alkenyl succinimide or succinimide ashless dispersant with a phosphorus ester or with an inorganic phosphorus-containing acid or anhydride and a boron compound.

2. Additional Antioxidant Compounds

Other antioxidant may be used in the compositions of the present invention, if desired. Typical antioxidants include hindered phenolic antioxidants, secondary aromatic amine antioxidants, hindered amine antioxidants, sulfurized phenolic antioxidants, oil-soluble copper compounds, phosphorus-containing antioxidants, organic sulfides, disulfides and polysulfides and the like.

Illustrative sterically hindered phenolic antioxidants include orthoalkylated phenolic compounds such as 2,6-di-tert-butylphenol, 4-methyl-2,6-di-tert-butylphenol, 2,4,6-tri-tert-butylphenol, 2-tert-butylphenol, 2,6-disopropylphenol, 2-methyl-6-tert-butylphenol, 2,4-dimethyl-6-tert-butylphenol, 4-(N,N-dimethylaminomethyl)-2,8-di-tert-butylphenol, 4-ethyl-2,6-di-tert-butylphenol, 2-methyl-6-styrylphenol, 2,6-distyryl-4-nonylphenol, and their analogs and homologs. Mixtures of two or more such mononuclear phenolic compounds are also suitable.

Other preferred phenol antioxidants for use in the compositions of this invention are methylene-bridged alkylphenols, and these can be used singly or in combinations with each other, or in combinations with sterically hindered un-bridged phenolic compounds. Illustrative methylene-bridged compounds include 4,4'-methylenebis(6-tert-butyl o-cresol), 4,4'-methylenebis(2-tert-amyl-o-cresol), 2,2'-methylenebis(4-methyl-6-tert-butylphenol), 4,4'-methylenebis(2,6-di-tert-butylphenol) and similar compounds. Particularly preferred are mixtures of methylene-bridged alkylphenols such as are described in U.S. Pat. No. 3,211,652, which is incorporated herein by reference.

Amine antioxidants, especially oil-soluble aromatic secondary amines may also be used in the compositions of this invention. Although aromatic secondary monoamines are preferred, aromatic secondary polyamines are also suitable. Illustrative aromatic secondary monoamines include diphenylamine, alkyl diphenylamines containing 1 or 2 alkyl substituents each having up to about 16 carbon atoms, phenyl-.beta.-naphthylamine, phenyl-p-naphthylamine, alkyl- or aralkyl-substituted phenyl-.beta.-naphthylamine containing one or two alkyl or aralkyl groups each having up to about 16 carbon atoms, alkyl- or aralkyl-substituted phenyl-p-naphthylamine containing one or two alkyl or aralkyl groups each having up to about 16 carbon atoms, and similar compounds.

A preferred type of aromatic amine antioxidant is an alkylated diphenylamine of the general formula:

$$R_5—C_6H_4—NH—C_6H_4—R_6 \qquad (2)$$

where $R^5$ is an alkyl group (preferably a branched alkyl group) having 8 to 12 carbon atoms, (more preferably 8 or 9 carbon atoms) and $R^6$ is a hydrogen atom or an alkyl group (preferably a branched alkyl group) having 8 to 12 carbon atoms, (more preferably 8 or 9 carbon atoms). Most preferably, $R^5$ and $R^6$ are the same. One such preferred compound is available commercially as Naugalube® 438L, a material which is understood to be predominately a 4,4'-dinonyldiphenylamine (i.e., bis(4-nonylphenyl)(amine)) in which the nonyl groups are branched.

The hindered amines are another type aminic antioxidants that may be used in compositions of this invention with two predominating types, the pyrimidines and piperidines. These are all described in great detail above, and in U.S. Pat. No. 5,073,278, U.S. Pat. No. 5,273,669, and U.S. Pat. No. 5,268, 113. Preferred hindered amines include 4-stearoyloxy-2,2,6, 6-tetramethylpiperidine and dodecyl-N-(2,2,6,6,-tetramethyl-4-piperidinyl)succinate, sold under the trade names Cyasorb® UV-3853 and Cyasorb® UV-3581 from Cytec, di(2,2,6,6-tetramethylpiperidin-4-yl) sebacate and di(1,2,2, 6,6-pentamethylpiperidin-4-yl) sebacate, sold as Songlight® 7700 and Songlight® 2920LQ from Songwon, and bis(1-octyloxy-2,2,6,-tetramethyl-4-piperidyl) sebacate, sold as Tinuvin® 123 by Ciba.

Another useful type of antioxidant for preferred inclusion in the compositions of the invention are one or more liquid, partially sulfurized phenolic compounds such as are prepared by reacting sulfur monochloride with a liquid mixture of phenols—at least about 50 weight percent of which mixture of phenols is composed of one or more reactive, hindered phenols—in proportions to provide from about 0.3 to about 0.7 gram atoms of sulfur monochloride per mole of reactive, hindered phenol so as to produce a liquid product. Typical phenol mixtures useful in making such liquid product compositions include a mixture containing by weight about 75% of 2,6-di-tert-butylphenol, about 10% of 2-tert-butylphenol, about 13% of 2,4,6-tri-tert-butylphenol, and about 2% of 2,4-di-tert-butylphenol. The reaction is exothermic and thus is preferably kept within the range of about 15° C. to about 70° C., most preferably between about 40° C. to about 60° C.

Another useful type of antioxidant are 2,2,4-trimethyl-1,2-dihydroquinoline (TMDQ) polymers and homologs containing aromatized terminal units such as those described in U.S. Pat. No. 6,235,686, which is hereby incorporated by reference.

Sulfur containing materials such as the methylene bis(dialkyldithiocarbamates) wherein the alkyl group contains 4 to 8 carbon atoms are useful antioxidants. For example, methylenebis(dibutyldithiocarbamate) is commercially available as VANLUBE 7723® from R. T. Vanderbilt Co., Inc).

Mixtures of different antioxidants may also be used. One suitable mixture is comprised of a combination of: (i) an oil-soluble mixture of at least three different sterically hindered tertiary butylated monohydric phenols, which is in the liquid state at 25° C.; (ii) an oil-soluble mixture of at least three different sterically-hindered, tertiary butylated methylene-bridged polyphenols; and (iii) at least one bis(4-alkylphenyl)amine wherein the alkyl group is a branched alkyl group having 8 to 12 carbon atoms, the proportions of (i), (ii) and (iii) on a weight basis falling in the range of 3.5 to 5.0 parts of component (i) and 0.9 to 1.2 parts of component (ii) per part by weight of component (iii), as disclosed in U.S. Pat. No. 5,328,619, which is incorporated herein by reference.

Other useful preferred antioxidants are those included in the disclosure of U.S. Pat. No. 4,031,023, which is herein incorporated by reference.

3. Seal Swell Compositions

Compositions that are designed to keep seals pliable are also well known in the art. A preferred seal swell composition is isodecyl sulfolane. The seal swell agent is preferably incorporated into the composition at about 0.1-3 weight percent. Substituted 3-alkoxysulfolanes are disclosed in U.S. Pat. No. 4,029,587, which is incorporated herein by reference.

4. Friction Modifiers

Friction modifiers are also well known to those skilled in the art. A useful list of friction modifiers is included in U.S. Pat. No. 4,792,410, which is incorporated herein by reference. U.S. Pat. No. 5,110,488 discloses metal salts of fatty acids and especially zinc salts and is incorporated herein by reference. Useful friction modifiers include fatty phosphites, fatty acid amides, fatty epoxides, borated fatty epoxides, fatty amines, glycerol esters, borated glycerol esters alkoxylated fatty amines, borated alkoxylated fatty amines, metal salts of fatty acids, sulfurized olefins, fatty imidazolines, molybdenum dithiocarbamates (e.g., U.S. Pat. No. 4,259,254, incorporated herein by reference), molybdate esters (e.g., U.S. Pat. No. 5,137,647 and U.S. Pat. No. 4,889,647, both incorporated herein by reference), molybdate amine with sulfur donors (e.g., U.S. Pat. No. 4,164,473 incorporated herein by reference), and mixtures thereof.

The preferred friction modifier is a borated fatty epoxide as previously mentioned as being included for its boron content. Friction modifiers are preferably included in the compositions in the amounts of 0.1-10 weight percent and may be a single friction modifier or mixtures of two or more.

Friction modifiers also include metal salts of fatty acids. Preferred cations are zinc, magnesium, calcium, and sodium and any other alkali or alkaline earth metals may be used. The salts may be overbased by including an excess of cations per equivalent of amine. The excess cations are then treated with carbon dioxide to form the carbonate. The metal salts are prepared by reacting a suitable salt with the acid to form the salt, and where appropriate adding carbon dioxide to the reaction mixture to form the carbonate of any cation beyond that needed to form the salt. A preferred friction modifier is zinc oleate.

5. Extreme Pressure/Antiwear Agents

Dialkyl dithiophosphate succinates may be added to provide antiwear protection. Zinc salts are preferably added as zinc salts of dihydrocarbyl phosphorodithioic acids and may be represented by the following formula:

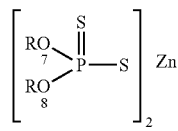

wherein $R_7$ and $R_8$ may be the same or different hydrocarbyl radicals containing from 1 to 18, preferably 2 to 12, carbon atoms and including radicals such as alkyl, alkenyl, aryl, arylalkyl, alkaryl and cycloaliphatic radicals. Particularly, preferred $R_7$ and $R_8$ groups are alkyl groups of 2 to 8 carbon atoms. Thus, the radicals may, for example, be ethyl, n-propyl, i-propyl, n-butyl, i-butyl, sec-butyl, amyl, n-hexyl, i-hexyl, n-octyl, decyl, dodecyl, octadecyl, 2-ethylhexyl, phenyl, butylphenyl, cyclohexyl, methylcyclopentyl, propenyl, butenyl. In order to obtain oil solubility, the total number of carbon atoms (i.e. R and R') in the dithiophosphoric acid will generally be about 5 or greater.

Also included in lubricating compositions in the same weight percent range as the zinc salts to give antiwear/extreme pressure performance are dibutyl hydrogen phosphite (DBPH) and triphenyl monothiophosphate, and the thiocarbamate ester formed by reacting dibutyl amine, carbon disulfide and the methyl ester of acrylic acid. The thiocarbamate is described in U.S. Pat. No. 4,758,362 and the phosphorus-containing metal salts are described in U.S. Pat. No. 4,466,894. Both patents are incorporated herein by reference. Antimony or lead salts may also be used for extreme pressure. The preferred salts are of dithiocarbamic acid such as antimony diamyldithiocarbamate.

6. Viscosity Modifiers

Viscosity modifiers (VM) and dispersant viscosity modifiers (DVM) are well known. Examples of VMs and DVMs are polymethacrylates, polyacrylates, polyolefins, styrene-maleic ester copolymers, and similar polymeric substances including homopolymers, copolymers and graft copolymers. Summaries of viscosity modifiers can be found in U.S. Pat. Nos. 5,157,088, 5,256,752 and 5,395,539, which are incorporated herein by reference. The VMs and/or DVMs preferably are incorporated into the fully formulated compositions at a level of up to 10% by weight.

7. Pour Point Depressants (PPD)

These components are particularly useful to improve low temperature qualities of lubricating oils. A preferred pour point depressant is an alkylnaphthalene. Pour point depressants are disclosed in U.S. Pat. Nos. 4,880,553 and 4,753,745, which are incorporated herein by reference. PPDs are commonly applied to lubricating compositions to reduce viscosity measured at low temperatures and low rates of shear. The pour point depressants are preferably used in the range of 0.1-5 weight percent. Examples of tests used to access low temperature, low shear rate rheology of lubricating fluids include ASTM D97 (pour point), ASTM D2983 (Brookfield viscosity), D4684 (Mini-rotary Viscometer) and D5133 (Scanning Brookfield).

8. Detergents

Lubricating compositions in many cases also preferably include detergents. Detergents as used herein are preferably metal salts of organic acids. The organic acid portion of the detergent is preferably a sulphonate, carboxylate, phenate, or salicylate. The metal portion of the detergent is preferably an alkali or alkaline earth metal. Preferred metals are sodium, calcium, potassium and magnesium. Preferably, the detergents are overbased, meaning that there is a stoichiometric excess of metal over that needed to form the neutral metal salt.

Preferred overbased organic salts are the sulfonate salts having a substantially oleophilic character and which are formed from organic materials. Organic sulfonates are well known materials in the lubricant and detergent arts. The sulfonate compound should preferably contain on average from about 10 to about 40 carbon atoms, more preferably from about 12 to about 36 carbon atoms and most preferably from about 14 to about 32 carton atoms on average. Similarly, the phenates, oxylates and carboxylates preferably have a substantially oleophilic character.

While the present invention allows for the carbon atoms to be either aromatic or in paraffinic configuration, it is highly preferred that alkylated aromatics be employed. While naphthalene based materials may be employed, the aromatic of choice is the benzene moiety.

The one particularly preferred component is thus an overbased monosulfonated alkylated benzene, and is preferably the monoalkylated benzene. Preferably, alkyl benzene fractions are obtained from still bottom sources and are mono- or di-alkylated compounds. It is believed, in the present invention, that the mono-alkylated aromatics are superior to the dialkylated aromatics in overall properties.

It is preferred that a mixture of mono-alkylated aromatics (benzene) be utilized to obtain the mono-alkylated salt (benzene sulfonate) in the present invention. The mixtures wherein a substantial portion of the composition contains polymers of propylene as the source of the alkyl groups assist in the solubility of the salt. The use of monofunctional (e.g., mono-sulfonated) materials avoids crosslinking of the molecules with less precipitation of the salt from the lubricant. It is preferred that the salt be overbased. The excess metal from overbasing has the effect of neutralizing acids, which may build up in the lubricant. A second advantage is that the overbased salt increases the dynamic coefficient of friction. Preferably, the excess metal will be present over that which is required to neutralize the acids at about in the ratio of up to about 30:1, preferably 5:1 to 18:1 on an equivalent basis.

The amount of the overbased salt utilized in the composition is preferably from about 0.1 to about 10 weight percents on an oil free basis. The overbased salt is usually made up in about 50% oil with a TBN range of 10-600 on an oil free basis. Borated and non-borated overbased detergents are described in U.S. Pat. Nos. 5,403,501 and 4,792,410, which are herein incorporated by reference for disclosure pertinent hereto.

9. Phosphates

The lubricating compositions can also preferably include at least one phosphorus acid, phosphorus acid salt, phosphorus acid ester or derivative thereof including sulfur-containing analogs preferably in the amount of 0.002-1.0 weight percent. The phosphorus acids, salts, esters or derivatives thereof include compounds selected from phosphorus acid esters or salts thereof, phosphites, phosphorus-containing amides, phosphorus-containing carboxylic acids or esters, phosphorus containing ethers and mixtures thereof In one embodiment, the phosphorus acid, ester or derivative can be a phosphorus acid, phosphorus acid ester, phosphorus acid salt, or derivative thereof. The phosphorus acids include the phosphoric, phosphonic, phosphinic, and thiophosphoric acids including dithiophosphoric acid as well as the monothiophosphoric, thiophosphinic and thiophosphonic acids.

One class of compounds are adducts of O,O-dialkyl-phosphorodithioates and esters of maleic or fumaric acid. The compounds can be prepared by known methods as described in U.S. Pat. No. 3,359,203, as for example O,O-di(2-ethylhexyl)S-(1,2-dicarbobutoxyethyl)phosphorodithioate.

The dithiophosphoric acid esters of carboxylic acid esters are another class of compounds useful to the invention. Preferred are alkyl esters having 2 to 8 carbon atoms, as for example 3-[[bis(1-methylethoxy)phosphinothioyl]thio]propionic acid ethyl ester.

A third class of ashless dithiophosphates for use with the present invention includes:
(i) those of the formula

wherein $R^7$ and $R^8$ are independently selected from alkyl groups having 3 to 8 carbon atoms (commercially available as VANLUBE 7611M, from R. T. Vanderbilt Co., Inc.);
(ii) dithiophosphoric acid esters of carboxylic acid such as those commercially available as IRGALUBE® 63 from Ciba Geigy Corp.;
(iii) triphenylphosphorothionates such as those commercially available as IRGALUBE® TPPT from Ciba Geigy Corp.; and
Zinc salts are preferably added to lubricating compositions in amounts of 0.1-5 triphenylphosphorothionates wherein the phenyl group may be substituted by up to two alkyl groups. An example of this group, among others, is triphenyl-phosphorothionate available commercially as IRGALUBE® TPPT (manufactured by Ciba-Geigy Corp.).

A preferred group of phosphorus compounds are dialkyphosphoric acid mono alkyl primary amine salts, such as those described in U.S. Pat. No. 5,354,484, which is herein incorporated by reference. Eighty-five percent phosphoric acid is the preferred compound for addition to the fully formulated ATF package and is preferably included at a level of about 0.01-0.3 weight percent based on the weight of the ATF.

The amine salts of alkyl phosphates are prepared by known methods, e.g., a method disclosed in U.S. Pat. No. 4,130,494, incorporated herein by reference. A suitable mono- or diester of phosphoric acid or their mixtures is neutralized with an amine. When monoester is used, two moles of the amine will be required, while the diester will require one mole of the amine. In any case, the amount of amine required can be controlled by monitoring the neutral point of the reaction where the total acid number is essentially equal to the total base number. Alternately, a neutralizing agent such as ammonia or ethylenediamine can be added to the reaction.

The preferred phosphate esters are aliphatic esters, among others, 2-ethylhexyl, n-octyl, and hexyl mono- or diesters. The amines can be selected from primary or secondary amines. Particularly preferred are tert-alkyl amines having 10 to 24 carbon atoms. These amines are commercially available as, for example, Primene® 81R manufactured by Rohm and Haas Co.

The sulfonic acid salts are well known in the art and are available commercially. Representative of the aromatic sulfonic acids that can be used in preparing the synergists of the invention are alkylated benzenesulfonic acids and alkylated naphthalenesulfonic acids having 1 to 4 alkyl groups of 8 to 20 carbons each. Particularly preferred are naphthalenesulfonates substituted by alkyl groups having 9 to 18 carbons each, as for example dinonylnaphthalenesulfonate.

10. Antifoamants

Antifoaming agents are well known in the art as silicone or fluorosilicone compositions. Such antifoam agents are available from Dow Corning Chemical Corporation and Union Carbide Corporation. A preferred fluorosilicone antifoam product is Dow FS-1265. Preferred silicone antifoam products are Dow Corning DC-200 and Union Carbide UC-L45. Other antifoam agents which may be included in the composition either alone or in admixture is a polyacrylate antifoamer available from Monsanto Polymer Products Co. of Nitro, W. Va. known as PC-1244. Also, a siloxane polyether copolymer antifoamer available from OSI Specialties, Inc. of Farmington Hills, Mich. may also be included. One such material is sold as SILWET-L-7220. The antifoam products are preferably included in the compositions of this invention at a level of 5 to 80 parts per million with the active ingredient being on an oil-free basis.

11. Rust Inhibitors

Embodiments of rust inhibitors include metal salts of alkylnapthalenesulfonic acids.

12. Copper Corrosion Inhibitors

Embodiments of copper corrosion inhibitors that may optionally be added include thiazoles, triazoles and thiadiazoles. Example embodiments of such compounds include benzotriazole, tolyltriazole, octyltriazole, decyltriazole, dodecyltriazole, 2-mercapto-benzothiazole, 2,5-dimercapto-1,3,4-thiadiazole, 2-mercapto-5-hydrocarbylthio-1,3,4-thiadiazoles, 2-mercapto-5-hydrocarbyldithio-1,3,4-thiadiazoles, 2,5-bis(hydrocarbylthio)-1,3,4-thiadiazoles, and 2,5-bis(hydrocarbyldithio)-1,3,4-thiadiazoles.

EXAMPLES

The following examples are given for the purpose of illustrating the invention and are not intended to limit the invention. All percentages and parts are based on weight unless otherwise indicated.

Example 1

Inventive and comparative MoDTC compositions were prepared using DTDA compositions as listed in Table 1. For inventive example (MoDTC-1), most of DTDA feed (DTDA-1) was derived from butylene feedstock containing about 70% 2-butylene (cis and trans), about 20% isobutylene and about 10% isobutylene. For comparative examples (MoDTC-A and MoDTC-B), DTDA feeds (DTDA-A and DTDA-B) were derived from propylene rich feedstock also containing either isobutylene or ethylene respectively. All MoDTC compositions were produced by the same procedure involving the reaction of the DTDA with molybdenum trioxide, water and carbon disulfide. Specifically, MoDTC compositions were prepared using methods taught in U.S. Pat. No. 7,312,348, incorporated herein by reference.

TABLE 1

| Sample | DTDA | DTDA Carbon Number Distribution, mass % | | | |
|---|---|---|---|---|---|
| | | C11 | C12 | C13 | C14 |
| MoDTC-1 (Inventive) | 95 mass % DTDA-1<br>5 mass % DTDA-B | trace<br>3 | <1<br>31 | >98<br>57 | trace<br>9 |
| MoDTC-A (Comparative) | 100 mass % DTDA-A | <1 | 22 | 70 | 8 |
| MoDTC-B (Comparative) | 100 mass % DTDA-B | 3 | 31 | 57 | 9 |

Example 2

MoDTC compositions of Examples 1 were completely dissolved in 4 cSt PAO synthetic base oil by heating 70° C. with good stirring. The solutions were allowed to cool to room temperature. After sitting at room temperature for period of 12 hours, the solutions were observed for precipitate. As summarized in Table 2, only the solution prepared with the inventive MoDTC-1 was free of precipitate.

Example 3

MoDTC compositions of Examples 1 were completely dissolved in commercial GF-4 conventional 10W-30 engine oil. The solutions were then placed in refrigerator maintained at 12° C. After 24 hours, the solutions were observed for precipitate. As summarized in Table 2, only the solution prepared with the inventive MoDTC-1 was free of precipitate.

Example 4

MoDTC compositions of Examples 1 were completely dissolved in commercial GF-4 synthetic 10W-30 engine oil. The solutions were then placed in freezer maintained at −10° C. After 6 and 60 days, the solutions were observed for precipitate. As summarized in Table 2, only the solution prepared with the inventive MoDTC-1 was free of precipitate.

TABLE 2

Storage Stability of MoDTC's in Different Lubricant Compositions

| Lubricant | Treat, mass %** | Temp. | Time | MoDTC-1* | MoDTC-A* | MoDTC-B* |
|---|---|---|---|---|---|---|
| 4 cSt PAO | 0.5 | RT | 12 h | Clear | ppt. | ppt. |
| Conventional GF-4 10W-30 Engine Oil | 1.0 | 12° C. | 24 h | Clear | ppt. | ppt. |
| Synthetic GF-4 10W-30 Engine Oil | 1.0 | −10° C. | 6 days/<br>60 days | Clear/<br>Clear | ppt./<br>heavy ppt. | ppt./<br>heavy ppt. |

*The MoDTC/diluent oil mixtures contain 7% by mass molybdenum measured as part of the MoDTC/diluent oil composition
**MoDTC is added to the lubricant as a 50/50 by mass mixture with a diluent oil, resulting in 0.25-0.5% MoDTC in the lubricant.

As per the examples, the inventive MoDTC prepared using major amount of DTDA derived from butylene feed stock was superior to MoDTC compositions prepared from DTDA compositions that were derived from propylene rich feed stocks. For those familiar with the art, these results are more surprising considering that MoDTC compositions produced from dialkylamines with wider carbon number distributions, i.e. propylene based DTDA, are expected to have better oil solubility than MoDTC compositions with very uniform carbon number distributions, i.e. butylene based DTDA. As per Table 1, alkyl chains for butylene based DTDA, DTDA-1, are essentially all iso-tridecyl while the alkyl chains of the propylene based DTDA compositions have carbon number range of 11 to 14 carbons. In retrospect, the excellent oil solubility of inventive MoDTC-1, wherein approximately 98% of the alkyl chains are $C_{13}$, can be attributed to isomeric diversity of butylene based DTDA, which in turn is ascribed to isomeric richness of butylene feedstock that contains 4 isomers, cis-2-butylene, trans-2-butylene, 1-butylene and isobutylene, while feedstocks for propylene derived DTDA contain no isomeric materials.

Example 5

Inventive and comparative MoDTC compositions were prepared using DTDA compositions as listed in Table 3. For inventive example (MoDTC-2), most of DTDA feed (DTDA-1) was derived from butylene feedstock containing about 70% 2-butylene (cis and trans), about 20% isobutylene and about 10% isobutylene. For comparative examples MoDTC-C, DTDA feed is a blend consisting of 70% DTDA-1 and 30% DTDA-B. The latter is derived from propylene rich feedstock also containing ethylene. For comparative examples MoDTC-D, DTDA feed is 100% DTDA-B. All MoDTC compositions were produced by the same procedure involving the reaction of the DTDA with molybdenum trioxide, water and carbon disulfide. Specifically, MoDTC compositions were prepared using methods taught in U.S. Pat. No. 7,524,799, incorporated herein by reference.

TABLE 3

| Sample | DTDA | DTDA Carbon Number Distribution, mass % | | | |
|---|---|---|---|---|---|
| | | C11 | C12 | C13 | C14 |
| MoDTC-2 (Inventive) | 95 mass % DTDA-1<br>5 mass % DTDA-B | trace<br>3 | <1<br>31 | >98<br>57 | trace<br>9 |

TABLE 3-continued

| Sample | DTDA | C11 | C12 | C13 | C14 |
|---|---|---|---|---|---|
| MoDTC-C (Comparative) | 70 mass % DTDA-1 30 mass % DTDA-B | trace 3 | <1 31 | >98 57 | trace 9 |
| MoDTC-D (Comparative) | 100 mass % DTDA-B | 3 | 31 | 57 | 9 |

Example 6

MoDTC compositions of Example 5 (0.73 mass percent) were completely dissolved in commercial conventional GF-5 5W-30 engine oil. The solutions were then placed in refrigerator maintained at 12° C. and in freezer maintained at −10° C. As summarized in Table 4, the only solutions that remained free of haze, cloudiness or precipitate after 40 days contained inventive MoDTC-2.

TABLE 4

Storage Stability of MoDTC compositions **(0.73%) in Conventional GF-5 5W-30 engine oil

| Temperature | MoDTC-2 | MoDTC-C | MoDTC-D |
|---|---|---|---|
| 12° C. | Clear at 40 days | Precipitate at 9 days | Precipitate at 1 day |
| −10° C. | Clear at 40 days | Very hazy at 2 days | Cloudy at 1 day |

**MoDTC is added to the lubricant as a 70/30 by mass mixture with a diluent oil, resulting in about 0.51% MoDTC in the lubricant.
The MoDTC/diluent oil mixtures contain about 9.6% by mass molybdenum measured as part of the MoDTC/diluent oil composition Example 7

MoDTC compositions of Examples 5 (0.73 mass percent) were completely dissolved in commercial synthetic GF-5 5W-30 engine oil. The solutions were then placed in refrigerator maintained at 12° C. and in freezer maintained at −10° C. As summarized in Table 5, the only solutions that remained free heavy haziness, cloudiness or precipitate after 40 days contained inventive MoDTC-2.

TABLE 5

Storage Stability of MoDTC compositions (0.73%) in Synthetic GF-5 5W-30 engine oil**

| Temperature | MoDTC-2 | MoDTC-C | MoDTC-D |
|---|---|---|---|
| 12° C. | Clear after 40 days | Precipitate at 16 days | Precipitate at 2 day |
| −10° C. | Slight haze at 2 days & 40 days | Very hazy at 2 days | Cloudy at 1 day |

*The MoDTC/diluent oil mixtures contain about 9.6% by mass molybdenum measured as part of the MoDTC/diluent oil composition
**MoDTC is added to the lubricant as a 70/30 by mass mixture with diluent oil, resulting in about 0.51% MoDTC in the lubricant.

As per the examples, the inventive MoDTC prepared using major amount of DTDA derived from butylene feed stock was superior to MoDTC compositions prepared from DTDA compositions containing >5% propylene based DTDA. Furthermore, it can be seen that the presence of MoDTC which is outside of the inventive limitation (i.e. >98% $C_{13}$) may be tolerated to a certain extent without adverse impact (e.g. up to 10%, preferably up to 5%, of MoDTC derived from DTDA-B). However, amounts >10% or more of MoDTC derived from DTDA-B as part of the overall MoDTC component in the lubricant give rise to adverse effect on solubility. Hence, the inventive lubricating compositions have a $C_{11}$-$C_{14}$ MoDTC component which consists of greater than 90%, more preferably at least 95%, and preferably at least 99%, of the inventive MoDTC derived from DTDA-1 having greater than 98% $C_{13}$. It is contemplated that the skilled person may wish to combine additional MoDTC, other than the C11-C14 type, as part of the inventive lubricating composition. That is, MoDTCs derived from ethylhexylamine or di-octyl amine, for example, may be added.

What is claimed is:

1. A method for producing a molybdenum dithiocarbamate composition, comprising the steps of:
    preparing a di-tridecylamine (DTDA) intermediate from a butylene feedstock comprising greater than 50% 2-butylene, and
    preparing a molybdenum dithiocarbamate composition from the DTDA intermediate.

2. The method of claim 1, wherein the butylene feedstock further comprises 1-butylene and isobutylene.

3. The method of claim 2, wherein the butylene feedstock comprises about 70% 2-butylene, about 20% 1-butylene and about 10% isobutylene.

4. The method of claim 3, wherein the molybdenum dithiocarbamate composition has, on average, greater than 98% $C_{13}$ as part of the substituent alkyl groups.

5. A method for preparing a lubricating composition, comprising the steps of:
    preparing a di-tridecylamine (DTDA) intermediate from a butylene feedstock comprising greater than 50% 2-butylene,
    preparing a molybdenum dithiocarbamate composition from the DTDA intermediate, and
    adding the molybdenum dithiocarbamate to a lubricating base at 0.01-3% of the lubricating composition.

* * * * *